United States Patent [19]
Heller et al.

[11] Patent Number: 5,939,453
[45] Date of Patent: Aug. 17, 1999

[54] PEG-POE, PEG-POE-PEG, AND POE-PEG-POE BLOCK COPOLYMERS

[75] Inventors: Jorge Heller, Woodside; Steven Y. Ng, San Francisco, both of Calif.

[73] Assignee: Advanced Polymer Systems, Inc., Redwood City, Calif.

[21] Appl. No.: 09/090,648

[22] Filed: Jun. 4, 1998

[51] Int. Cl.$^6$ .................. A61K 31/335; A61K 47/34; C07D 319/08
[52] U.S. Cl. .................. 514/452; 514/456; 514/772.1; 549/335
[58] Field of Search .................. 514/452, 456, 514/772.1; 549/335

[56] References Cited

U.S. PATENT DOCUMENTS

| | | | |
|---|---|---|---|
| 4,304,767 | 12/1981 | Heller et al. | 424/78 |
| 4,532,335 | 7/1985 | Helwing | 549/335 |
| 4,946,931 | 8/1990 | Heller et al. | 528/230 |
| 4,957,998 | 9/1990 | Heller et al. | 528/220 |
| 5,133,739 | 7/1992 | Bezwada et al. | 606/230 |
| 5,412,072 | 5/1995 | Sakurai et al. | 530/322 |
| 5,449,513 | 9/1995 | Yokoyama et al. | 424/78.08 |
| 5,510,103 | 4/1996 | Yokoyama et al. | 424/78.08 |
| 5,518,730 | 5/1996 | Fuisz | 424/426 |
| 5,620,697 | 4/1997 | Törmälä et al. | 424/426 |
| 5,622,718 | 4/1997 | Al-Shamkhani et al. | 424/488 |
| 5,626,862 | 5/1997 | Brem et al. | 424/426 |
| 5,651,986 | 7/1997 | Brem et al. | 424/484 |
| 5,693,751 | 12/1997 | Sakurai et al. | 530/322 |

FOREIGN PATENT DOCUMENTS

97/25366  7/1997  WIPO.

OTHER PUBLICATIONS

R. Duncan et al., "The role of polymer conjugates in the diagnosis and treatment of cancer", *STP Pharma Sciences*, 6(4), 237–263 (1996).

J. Heller, "Poly(ortho esters)", *Adv. Polymer Sci.*, 107, 41–92 (1993).

G.S. Kwon et al., "Block copolymer micelles as long–circulating drug vehicles", *Adv. Drug Delivery Rev.*, 16, 295–309 (1995).

W.N.E. Wolthuis et al., "Synthesis and characterization of poly(ethylene glycol) poly(L–lactide) block copolymers", *Third Eur. Symp. Controlled Drug Delivery*, 271–276 (1994).

L. Youxin et al., "Synthesis and properties of biodegradable ABA triblock copolymers . . . ", *J. Controlled Release*, 27, 247–257 (1993).

*Primary Examiner*—Johann Richter
*Assistant Examiner*—Taofiq A. Solola
*Attorney, Agent, or Firm*—Heller Ehrman White & McAuliffe

[57] ABSTRACT

PEG-POE, PEG-POE-PEG, and POE-PEG-POE block copolymers have both hydrophilic and hydrophobic blocks. They form micelles in aqueous solution, making them suitable for encapsulation or solubilization of hydrophobic or water-insoluble materials; and they also form bioerodible matrices for the sustained release of active agents, especially when the POE block(s) contain at least one unit containing an α-hydroxy acid.

20 Claims, 1 Drawing Sheet

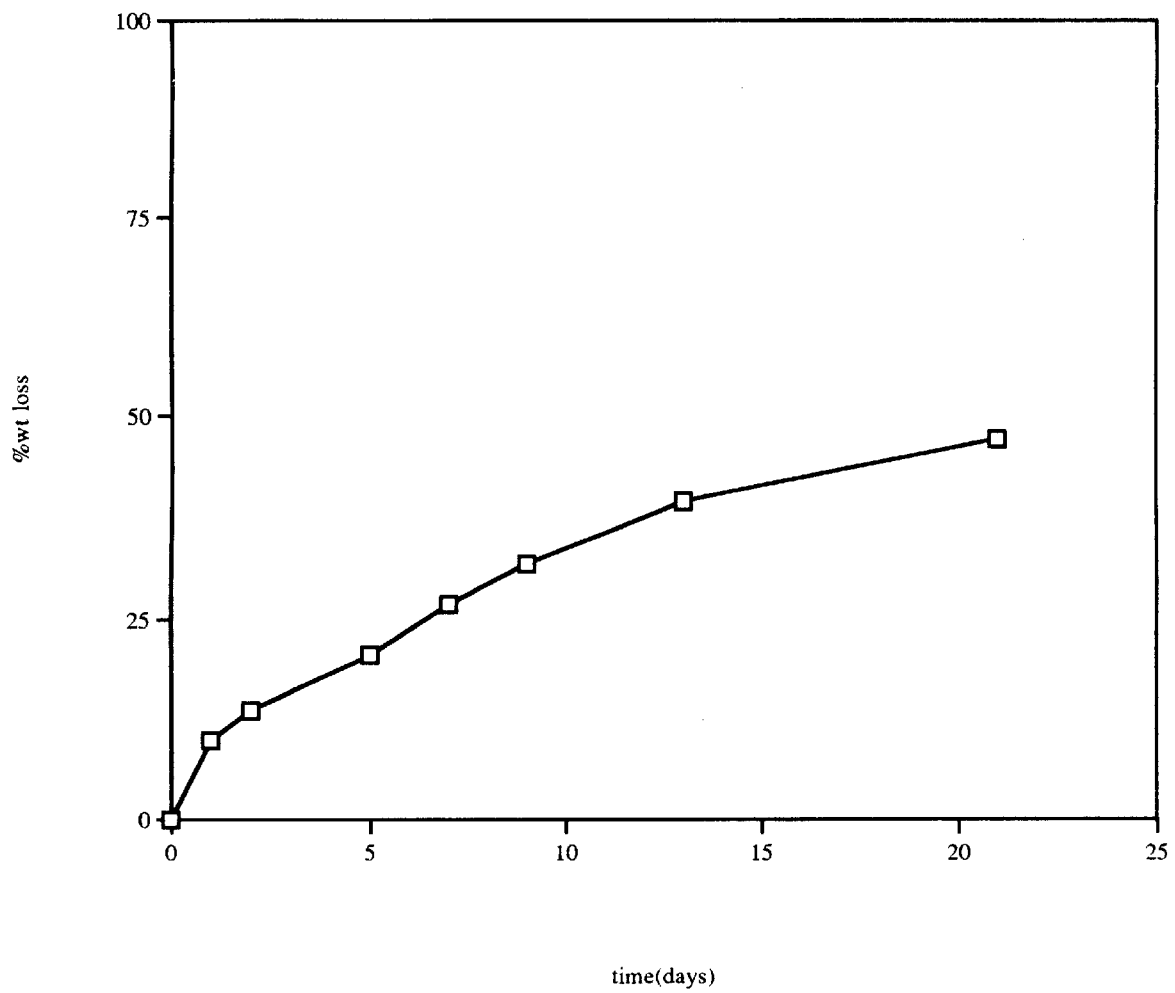

PEG-POE, PEG-POE-PEG, AND POE-PEG-POE BLOCK COPOLYMERS

BACKGROUND OF THE INVENTION

1. Field of the Invention

This invention relates to poly(ethylene glycol)-poly(orthoester), poly(ethylene glycol)-poly(orthoester)-poly(ethylene glycol), and poly(orthoester)-poly(ethylene glycol)-poly(orthoester) block copolymers.

2. Background to the Invention

1. Micellar System for Tumor Targeting

One of the major problems in treating cancer is the difficulty of achieving a sufficient concentration of an anticancer agent in the tumor. This is due to the toxicity, sometimes extreme, of such agents which severely limits the amounts that can be used. However, a major discovery in cancer chemotherapy has been the so-called EPR (enhanced permeation and retention) effect. The EPR effect is based on the observation that tumor vasculature, being newly formed vasculature, has an incompletely formed epithelium and is much more permeable than established older vasculature which is essentially impermeable to large molecules. Further, lymphatic drainage in tumors is very poor thus facilitating retention of anticancer agents delivered to the tumor.

The EPR effect can be used in cancer targeting by using delivery systems containing anticancer drugs that are too large to permeate normal vasculature, but which are small enough to permeate tumor vasculature, and two approaches have been developed. In one approach, a water-soluble polymer is used that contains an anticancer drug chemically bound to the polymer via a hydrolytically labile linkage. Such drug-polymer constructs are injected intravenously and accumulate in the tumors, where they are internalized by the cells via endocytosis and released in the lysosomal compartment of the cell via enzymatic cleavage of the labile bond attaching the drug to the polymer. Two disadvantages of this approach are that, first, nondegradable, water-soluble polymers have been used, and this requires a tedious fractionation of the polymer to assure that the molecular weight of the polymer is below the renal excretion threshold, and, second, the drug must be chemically attached to the polymer, which in effect creates a new drug entity with consequent regulatory hurdles that must be overcome. The use of polymer conjugates in cancer diagnosis and treatment is discussed in R. Duncan et al., "The role of polymer conjugates in the diagnosis and treatment of cancer", *S.T.P. Pharma Sciences*, 6(4), 237–263 (1996), and an example of an alginate -bioactive agent conjugate is given in Al-Shamkhani et al., U.S. Pat. No. 5,622,718.

An alternate approach has been described. In this approach, an AB or ABA block copolymer is prepared where the B-block is hydrophobic and the A-block is hydrophilic. When such a material is placed in water, it will self-assemble into micelles with a hydrophobic tore and a hydrophilic shell surrounding the core. Such micelles have a diameter of about 100 nm, which is large enough that when they are injected intravenously, the micelles can not leave the normal vasculature, but they are small enough to leave the vasculature within tumors. Further, a 100 nm diameter is too small to be recognized by the reticuloendothelial system, thus enhancing micelle lifetime within the blood stream. Additionally, when the hydrophilic block is poly(ethylene glycol), further enhancement of circulation time is noted, as has been observed with "stealth" liposomes. The use of block copolymer micelles is reviewed in G. S. Kwon et al., "Block copolymer micelles as long-circulating drug delivery vehicles", *Adv. Drug Delivery Rev.*, 16, 295–309 (1995).

Sakurai et al., U.S. Pat. Nos. 5,412,072 and 5,693,751, and Yokoyama et al., U.S. Pat. Nos. 5,449,513 and 5,510,103, describe block copolymers useful as micellar delivery systems where the hydrophilic block is poly(ethylene glycol) and the hydrophobic blocks are various derivatives of poly(aspartic acid), poly(glutamic acid) and polylysine. U.S. Pat. Nos. 5,412,072 and 5,693,751 describe an approach where drugs have been chemically attached to the hydrophobic segment; while U.S. Pat. Nos. 5,449,513 and 5,510,103 describe an approach where hydrophobic drugs have been physically entrapped within the hydrophobic portion of the micelle. This latter approach is clearly preferable because no chemical modification of the drug is necessary.

2. Bioerodible Block Copolymer Matrix for Controlled Drug Delivery

In AB, ABA, or BAB block copolymers comprising a hydrophilic A block and a hydrophobic B block, the A and B blocks are incompatible and on a microscopic scale will phase-separate. This phase separation imparts unique and useful thermal properties to the material.

There is considerable prior art in the development of block copolymers comprised of poly(ethylene glycol) and bioerodible hydrophobic segments such as poly(L-lactic acid), poly(L-lactic-co-glycolic acid) copolymers and poly(ε-caprolactone), and discussion of their use as drug delivery agents. For example, see W. N. E. Wolthuis et al., "Synthesis and characterization of poly(ethylene glycol) poly-L-lactide block copolymers", *Third European Symposium on Controlled Drug Delivery*, 271–276 (1994), L. Youxin et al., "Synthesis and properties of biodegradable ABA triblock copolymers . . . ", *J. Controlled Release*, 27, 247–257 (1993), and Bezwada et al., U.S. Pat. No. 5,133,739.

Poly(orthoesters) are known as potential vehicles for sustained release drug delivery. See, for example, J. Heller, "Poly (Ortho Esters)", *Adv. Polymer Sci.*, 107, 41–92 (1993), and references cited therein, Heller et al., U.S. Pat. Nos. 4,304,767, 4,946,931, and 4,957,998, and PCT International Publication No. WO97/25366.

The disclosures of these and other documents referred to in this application are incorporated herein by reference.

However, no block copolymer systems have been described where the hydrophobic, bioerodible segment is a poly(orthoester).

SUMMARY OF THE INVENTION

In a first aspect, this invention provides a block copolymer of formula I:

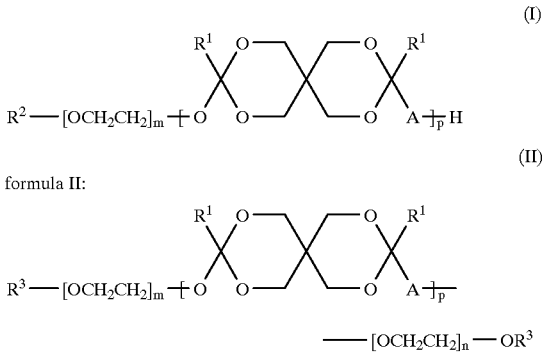

formula II:

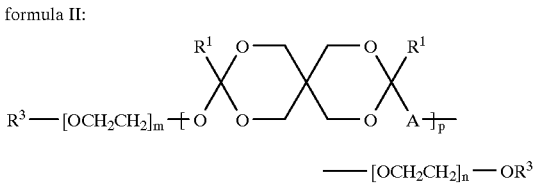

3

-continued or formula III:

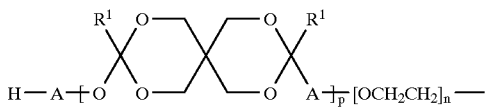

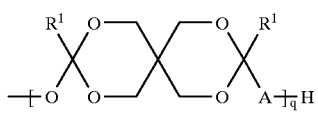

in which:.
m and n are independently an integer from 5 to 500;
p and q are independently an integer from 5 to 100;
$R^1$ and $R^2$ are independently $C_1$–$C_4$ alkyl;
$R^3$ is H or $C_1$–$C_4$ alkyl; and
A is —O—$R^4$—, —O—$R^5$—, or a mixture thereof, where:
$R^4$ is selected from

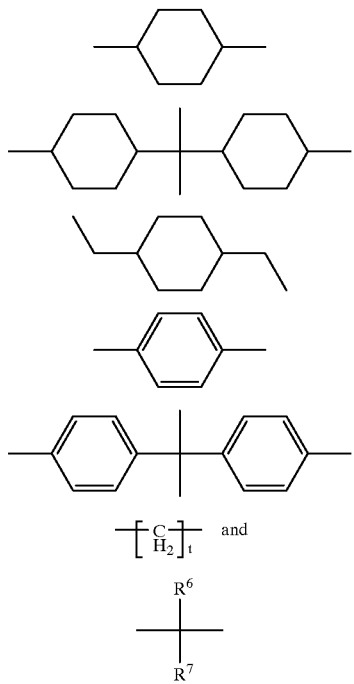

where t is an integer from 1 to 12,
$R^6$ is $C_1$–$C_4$ alkyl, and
$R^7$ is H or $C_1$–$C_4$ alkyl, and
$R^5$ is

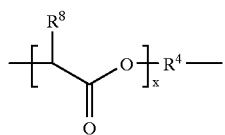

in which:
x is an integer from 1 to 10, and
$R^8$ is H or $C_1$–$C_6$ alkyl.

In a second aspect, this invention provides a process for the preparation of a block copolymer of formula I, formula II, or formula III, as described in the "DETAILED DESCRIPTION OF THE INVENTION".

In a third aspect, this invention provides a micellar pharmaceutical composition for the delivery of a hydrophobic or water-insoluble active agent, comprising the active agent physically entrapped within but not covalently bonded to a drug carrier comprising a block copolymer of formula I, formula II, or formula III, or a mixture thereof.

In a fourth aspect, this invention provides a composition for the sustained release of an active agent, comprising the active agent dispersed in a matrix comprising a block copolymer of formula I, formula II, or formula m, or a mixture thereof.

BRIEF DESCRIPTION OF THE DRAWING

The FIGURE shows the rate of weight loss of a block copolymer of this invention in aqueous solution.

DETAILED DESCRIPTION OF THE INVENTION

Definitions

Unless defined otherwise in this specification, all technical and scientific terms are used herein according to their conventional definitions as they are commonly used and understood by those of ordinary skill in the art of synthetic and pharmaceutical chemistry.

"Active agent" includes any compound or mixture of compounds which produces a beneficial or useful result. Active agents are distinguishable from such components as vehicles, carriers, diluents, lubricants, binders and other formulating aids, and encapsulating or otherwise protective components. Examples of active agents are pharmaceutical, agricultural or cosmetic agents., Suitable pharmaceutical agents include antigens, antibodies, vaccines, hormones (for example, estrogens, progestins, androgens, adrenocortical steroids, insulin, erythropoietin and the like), vitamins, enzymes, proteins, naturally occurring or bioengineered substances, anti-infectives (including antibiotics, antivirals, fungicides, scabicides or pediculicides), antipsychotic agents (for example, phenothiazines including chlorpromazine, triflupromazine, mesoridazine, piperacetazine and thioridazine; thioxanthenes including chlorprothixene; and the like), anti-anxiety agents (for example, benzodiazepines including diazepam, alprazolam, clonazepam, oxazepam; and barbiturates), anti-depressants (including tricyclics, monoamine oxidase inhibitors, serotonin reuptake inhibitors, and others, including imipramine, amitriptyline, doxepin, nortriptyline, amoxapine, tranylcypromine, phenelzine, and the like), stimulants (for example, methylphenidate, doxapram, nikethamide, and the like), narcotics (for example, morphine, meperidine, codeine, and the like), analgesic-antipyretics and anti-inflammatory agents (for example, aspirin, ibuprofen, naproxen, and the like), local anesthetics (for example, procaine, lidocaine, tetracaine, and the like), fertility control agents, anticancer agents (including the anthracycline antibiotics such as doxorubicin, daunorubicin, and epirubicin, mitomycin C, dactinomycin, tamoxifen, paclitaxel and its analogs such as docetaxol, platinum analogs such as cisplatin and carboplatin, anticancer proteins such as neocarzinostatin and L-asparaginase, photosensitizers for photodynamic therapy, alkylating agents such as cyclophosphamide, mechlorethamine, melphalan, chlorambucil, carmustine, and lomustine, antimetabolites such as methotrexate, alkaloids such as vinblastine, vincristine, and vindesine, 5-fluorouracil, thioguanine, streptozocin, bleomycin, and the like), cardiovascular and anti-hypertensive agents (for example, procainamide, amyl nitrite, nitroglycerin, propranolol, metoprolol, prazosin, phentolamine, trimethaphan, captopril, enalapril and the like), drugs for the therapy of pulmonary disorders, anti-epilepsy agents (for example, phenytoin, ethotoin and the like), antipruritics, astringents, anti-hidrotics, keratolytic agents, keratoplastic agents, rubefacients, sunscreens, pigmentation agents or emollients. The term "active agents" further includes biocides such as fungicides, pesticides, and herbicides, plant growth promoters or inhibitors, preservatives, disinfectants, air purifiers and nutrients.

"Bioerodible", "biodegradable", and the like terms refer to the degradation, disassembly or digestion of the polymer by action of a biological environment, including the action of living organisms, and most notably at physiological pH and temperature. A principal mechanism for bioerosion of the copolymers of the present invention is hydrolysis of linkages between and within the POE blocks of the copolymer.

"CDM" means cyclohexanedimethanol.

"Controlled release", "sustained release", and similar terms mean a mode of active agent delivery that occurs when the active agent is released from the vehicle or carrier at an ascertainable and controllable rate over a period of time, rather than dispersed immediately upon ingestion or application. Controlled or sustained release may extend for hours, days or months, and may vary as a function of numerous factors. In the present invention, an important determinant of the rate of delivery is the rate of hydrolysis of the linkages between and within the copolymer. The rate of hydrolysis in turn may be controlled by the composition of the copolymer and the number of hydrolyzable bonds in the copolymer. Other factors include particle size, particle composition, particle hydration, acidity of the medium (either internal or external to the matrix), solubility of the active agent in the matrix and molecular weight and charge density of the active agent.

"DETOSU" means 3,9-di(ethylidene)-2,4,8,10-tetraoxaspiro[5.5]undecane.

"Matrix" means the physical structure of the copolymer. Solid matrices essentially retain the active agent in a manner preventing release of the agent until the copolymer erodes or decomposes.

"PEG" means polyethylene glycol, H—[OCH$_2$CH$_2$]$_m$—OH, with a numerical suffix indicating the nominal number average molecular weight, M$_n$. Unless the context requires otherwise, "PEG" also includes polyethylene glycol C$_1$–C$_4$ alkyl ether, R$^2$—[OCH$_2$CH$_2$]$_m$—OH sometimes referred to as "RPEG".

"POE" means a poly(orthoester).

"PTSA" means p-toluenesulfonic acid.

"Sequestration" means the confinement or retention of an active agent within the internal spaces of a copolymer matrix. Sequestration of an active agent within the matrix may limit the toxic effect of the agent, prolong the time of action of the agent in a controlled manner, permit the release of the agent in a precisely defined location in an organism, or protect an unstable agent against the action of the environment.

"THF" means tetrahydrofuran.

"Vehicle" and "carrier" mean an ingredient that is included in a composition such as a pharmaceutical or cosmetic preparation for reasons other than a therapeutic or other biological effect. Functions served by vehicles and carriers include transporting an active agent to a site of interest, controlling the rate of access to, or release of, the active agent by sequestration or other means, and facilitating the application of the agent to the region where its activity is needed. The copolymers of this invention may serve as vehicles for the sustained release of active agents.

Ranges given, such as temperatures, times, sizes, and the like, should be considered approximate, unless specifically stated;

Ingredient names are taken from the *International Cosmetic Ingredient Handbook*, 3rd edition, 1995.

The Block Copolymers of this Invention

The block copolymers of this invention are of formula I:

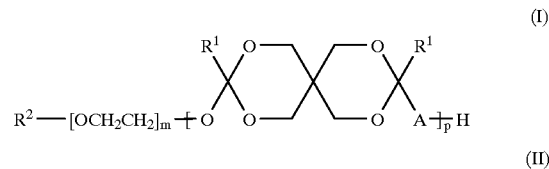

formula II:

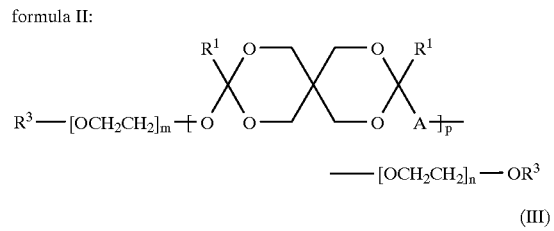

or formula III:

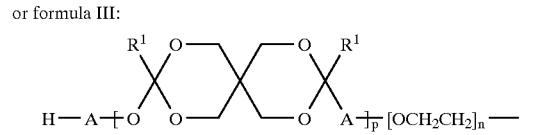

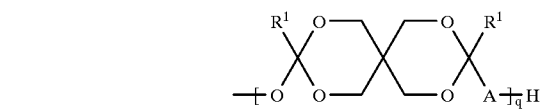

in which:

m and n are independently an integer from 5 to 500;
p and q are independently an integer from 5 to 100;
R$^1$ and R$^2$ are independently C$_1$–C$_4$ alkyl;
R$^3$ is H or C$_1$–C$_4$alkyl; and
A is —O—R$^4$—, —O—R$^5$—, or a mixture thereof, where:
R$^4$ is selected from

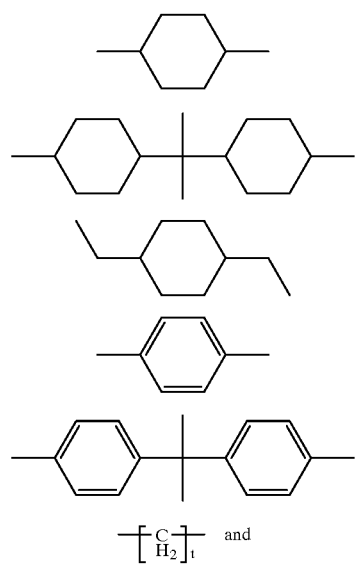

-continued

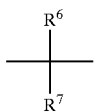

where t is an integer from 1 to 12,
$R^6$ is $C_1$–$C_4$ alkyl, and
$R^7$ is H or $C_1$–$C_4$ alkyl; and
$R^5$ is

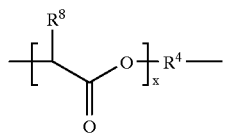

in which:
x is an integer from 1 to 10, and
$R^8$ is H or $C_1$–$C_6$ alkyl.

The copolymers are AB (formula I), ABA (formula II), and BAB (formula III) block copolymers in which the A blocks are hydrophilic poly(ethylene glycol) and the B blocks are hydrophobic poly(orthoester). Within these, the poly(orthoester) blocks are composed of alternating residues of a diketene acetal and a diol.

The properties of the copolymers, including both the mechanophysical properties and the bioerodibility, are determined by the type of the copolymer (whether AB diblock, ABA triblock, or BAB triblock), the length of the PEG and POE blocks, and the diol(s) used in the POE blocks (in particular, the proportion of diol of the general formula HO—$R^5$—OH used in the POE blocks).

Preferred polymers are those in which:
m and n are independently an integer from 50 to 250, especially when m and n are the same;
p and q are independently an integer from 10 to 50, especially when p and q are the same;
$R^1$ is ethyl;
$R^2$ is methyl;
$R^3$ is hydrogen or methyl, especially methyl;
$R^4$ is CDM;
the proportion of —O—$R^5$— groups in the molecule is from 0 to 10%; and
in each $R^5$ group x is 1 or 2 and $R^8$ is hydrogen or methyl.

While a block copolymer having any one of these preferences listed above is preferred over a block copolymer not having that preference, the block copolymers will be more preferred the greater the number of preferences met.

Because of the polymer character of these molecules, the number of repeating units within the blocks, m, n, p, and q, necessarily represent averages rather than exact numbers; and in particular, when m and n or p and q are described as being the same, this indicates that the average values of m and n, or of p and q, should be approximately the same.

The Starting Materials

Polyethylene glycols, and polyethylene glycol lower alkyl ethers of various chain lengths (molecular weights) are available from a number of sources, including Aldrich Chemical Company, Inc., Milwaukee, Wis., and Shearwater Polymers, Huntsville, Ala.

Diketene acetals of formula IV may be prepared, for example, by the methods described in J. Heller, "Poly (Ortho Esters)", *Adv. Polymer Sci.*, 107, 41–92 (1993), and references cited therein, or Helwing, U.S. Pat. No. 4,532,335. The preparation of DETOSU is described in Preparation 1 below.

Diols of the formula HO—$R^4$—OH are generally commercially available from such suppliers as Aldrich Chemical Company, Inc., Milwaukee, Wis., and other suppliers of organic chemicals. Trans-cyclohexanedimethanol is commercially available from Cros-Organics, New Jersey. The α-hydroxy acid containing diols of the formula HO—$R^5$—OH may be prepared by the reaction of a diol of the formula HO—$R^4$—OH with from 0.5 to 5 molar equivalents of a cyclic ester of an α-hydroxy acid, such as L-lactide or glycolide. Suitable reaction conditions are temperatures from 100° C. to 200° C. and times from 1 to 60 hours, especially from 12 to 48 hours. The reaction may be performed in the absence of solvent, or in the presence of aprotic polar solvents such as dimethylformamide, dimethylacetamide, dimethylsulfoxide, acetonitrile, and the like. The preparation of some representative α-hydroxy acid containing diols is described in Preparation 2 below. Alternative preparative techniques for the diols of the formula HO—$R^5$—OH such as partial esterification of a diol of the formula HO—$R^4$—OH with an (optionally protected) α-hydroxy acid, will also be apparent to a person of ordinary skill in the art having regard to this disclosure.

Preparation of the Block Copolymers

The diblock copolymers of formula I are prepared in a two-step synthesis. In the first step, a PEG lower alkyl ether of the formula $R^2$—[OCH$_2$CH$_2$]$_m$—OH, where $R^2$ is $C_1$–$C_4$ alkyl (an RPEG), is reacted with an excess of a diketene acetal of formula IV,

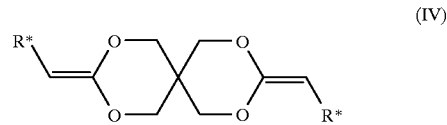

(IV)

to form an intermediate of formula V

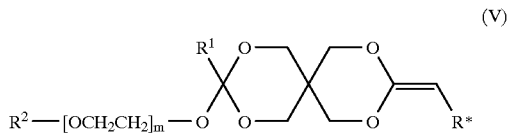

(V)

In the second step, a diol of the formula HO—$R^4$—OH, or HO—$R^5$—OH, or a mixture thereof, is reacted with the solution of the first step (containing the intermediate of formula IV and the excess diketene acetal) to extend the POE block, thereby forming the diblock copolymer of formula I.

Since the diketene acetal and the diol react in a 1:1 ratio to form the POE block of the diblock copolymer, the quantities of the RPEG, the diketene acetal, and the diol are chosen so that the molar amount of diketene acetal is equal to the sum of the molar amounts of the RPEG and the diol.

The value of m in the PEG block, i.e. the length of the PEG block, is determined by the RPEG chosen.

The value of n in the POE block, i.e. the length of the POE block, is determined by the molar quantity of diol relative to the molar quantity of RPEG: the greater the molar quantity of diol (assuming that the diketene acetal is present in at least an equimolar quantity), the longer is the POE block.

The triblock copolymers of formula II are also formed in a two-step synthesis. In the first step, an excess of the diketene acetal of formula IV is reacted with a diol of the formula HO—$R^4$—OH or HO—$R^5$—OH or a mixture thereof, to form a POE block which is terminated at each end with a diketene acetal unit, giving an intermediate of formula VI

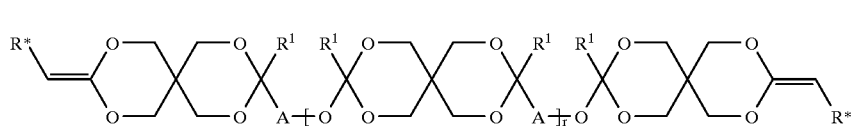

(VI)

where r is p-2.

In the second step, the intermediate of formula VI is reacted with two equivalents of PEG or an RPEG to form the triblock copolymer of formula II.

Since the diketene acetal and the diol react in essentially a 1:1 ratio to form the POE block of the triblock copolymer, but diketene acetal termination of the POE block is desired, the quantities of the diketene acetal and the diol are chosen so that the molar amount of diketene acetal is slightly greater than the molar amount of the diol. The molar ratio of PEG/RPEG to POE block should be approximately 2:1, but an excess of PEG/RPEG may be used, as it may be easily separated from the polymer after completion of the reaction.

The values of m and n for the PEG blocks, are determined by the PEG/RPEG chosen. Typically m and n are the same, when a single PEG/RPEG is used; but if two or more PEGs/RPEGs of different lengths are used, then mixtures of copolymers containing varying PEG block lengths can be obtained, and these mixtures may be separated if desired, by such molecular weight fractionation techniques as gel permeation chromatography.

The value of p for the POE block is determined primarily by the ratio of the diketene acetal to the diol used to form the POE.

The triblock copolymers of formula III are also formed in a two-step synthesis. In the first step, a PEG of the formula H—[OCH$_2$CH$_2$]$_m$—OH is reacted with an excess of a diketene acetal of formula IV to form an intermediate of formula VII

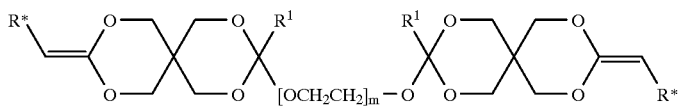

(VII)

In the second step, a diol of the formula HO—R$^4$—OH or HO—R$^5$—OH, or a mixture thereof, is reacted with the solution of the first step (containing the intermediate of formula VII and the excess diketene acetal) to extend the POE blocks, thereby forming the triblock copolymer of formula III.

Since the diketene acetal and the diol react in a 1:1 ratio to form the POE blocks of the diblock copolymer, the quantities of the PEG, the diketene acetal, and the diol are chosen so that the molar amount of diketene acetal is equal to the sum of the molar amounts of the PEG and the diol.

The value of m for the PEG block is determined by the PEG chosen.

The values of p and q for the POE blocks are determined by the molar quantity of diol relative to the molar quantity of PEG: the greater the molar quantity of diol (assuming that the diketene acetal is present in at least an equimolar quantity), the longer are the POE blocks. Typically the POE blocks will be of equal lengths, on average.

In an alternative synthesis of the triblock copolymer of formula III, POE blocks terminated with diketene acetal units (intermediates of formula VI) are prepared, and reacted with 0.5 molar equivalent of PEG to terminate each end of the PEG with the POE blocks.

In any of the syntheses in which the copolymers may have an unreacted diketene acetal terminal group, the copolymer may be reacted with a hydroxy-containing compound, such as a C$_1$–C$_4$ alcohol, to terminate the copolymer with alkoxy units; and such alkoxy-terminated copolymers are included within the scope of the invention. The hydroxy-containing compound, especially a C$_1$–C$_4$ alcohol, may be employed in excess and the unreacted excess easily separated during purification of the polymer.

Suitable reaction conditions for the formation of the copolymers are those conditions well known for the formation of orthoesters, such as are described in WO97/25366 and the other documents cited in the BACKGROUND OF THE INVENTION. Typically, the reaction takes place in a polar aprotic solvent, such as those solvents mentioned previously for the preparation of the a-hydroxy acid containing diols, and ethers, especially THF. A catalyst may be used if desired or necessary, and may be selected from those catalysts known to the art for the formation of orthoesters. Suitable such catalysts include iodine/pyridine, strong acids such as p-toluenesulfonic acid; Lewis acids, such as boron trichloride etherate, boron trifluoride etherate, tin oxychloride, phosphorus oxychloride, zinc chloride, phosphorus pentafluoride, antimony pentafluoride, stannic chloride, and the like; and Brönsted acids, such as polyphosphoric acid, polystyrenesulfonic acid, and the like. A particularly suitable catalyst is PTSA. A typical amount of catalyst used is about 0.2% by weight relative to the diketene acetal, though quantities between 0.005% and 2% may be used.

Suitable reaction temperatures are from room temperature to the boiling point of the solvent used, for example, between 20 C and 70° C.; and suitable reaction times are between a few minutes and 48 hours, typically between 30 minutes and 24 hours.

Once the formation of the block copolymer is complete, the copolymer can be isolated by precipitation in a non-polar aprotic solvent such as hexane. Typically, the reaction mixture containing the copolymer (which may be cooled before the addition) is added slowly to about ten volumes of the rapidly stirred solvent at room temperature. The precipitated block copolymer may be collected by filtration, decantation, or other suitable method, washed to remove unreacted monomers or other contaminants, and dried, typically in a vacuum oven at a temperature below its melting point.

The bioerodibility of a block copolymer of this invention is determined by two factors: first, the extent to which the copolymer will dissolve/become suspended intact in an aqueous medium, the solubility of the copolymer; and second, the extent to which the copolymer, or, to be more precise, the POE block(s), will degrade in the environment to which it is exposed. The speed of degradation of the POE block(s) of the copolymer in an aqueous environment is determined by the hydrophilicity of the copolymer and by the proportion of α-hydroxy acid ester groups, if present, in the block(s), with greater bioerodibility being achieved by inclusion of a greater proportion of diols of the formula HO—$R^5$—OH in the diol mixture used to form the POE block(s).

Uses of the Block Copolymers of this Invention

While the block copolymers of this invention will find utility in any of the uses for which biodegradable polymers are useful, including such uses as vehicles for the sustained release of active agents, orthopedic implants, degradable sutures, and the like, they will also find particular utility in applications where their nature as block copolymers having both hydrophobic and hydrophilic blocks confers a special benefit, and these uses will be addressed in greater detail, since a person of ordinary skill in the art will be well acquainted with the uses of biodegradable polymers and will have no difficulty, having regard to the skill of the art and this disclosure, in adapting the block copolymers of this invention to such uses.

1. Micellar System for Tumor Targeting

Polymers useful as micellar delivery systems can be prepared by forming diblock, AB, or triblock, ABA or BAB, copolymers comprising a hydrophilic poly(ethylene glycol) A block and a hydrophobic poly(orthoester) B block.

When such block copolymers are placed in water, in which the poly(ethylene glycol) block is soluble and the poly(orthoester) block is insoluble, the block copolymer chains will spontaneously self-aggregate to form micellar structures. The hydrodynamic diameter of such micelles, which may be determined by methods such as dynamic light scattering, will be in the order of 10–30 nm. As may be determined by methods such as static light scattering, such micelles will contain several hundred polymer chains. The micelles will undergo a secondary, reversible association, giving particles of an average diameter of about 100 nm. While such micelles are too large to be excreted by the kidneys, individual block copolymers are not. Further, since the poly(orthoester) segments can be made to be biodegradable, facile renal excretion will take place.

The major utility of such micellar systems resides in their ability to entrap and solubilize hydrophobic drugs in the hydrophobic core. Such entrapment is easily carried out in a number of ways. Thus, the drug can be added to the aqueous solution containing micelles and incorporated by simple stirring, by heating to moderate temperatures, or by ultrasonication. The micelles are efficient carriers for a variety of hydrophobic or insoluble active agents, and are particularly suitable as carriers for anticancer agents, which will accumulate in the tumor by an endocytotic process.

Efficient entrapment of hydrophobic drugs requires a highly hydrophobic core. Using AB, ABA, or BAB block copolymers where the hydrophobic B block forms a biodegradable, highly hydrophobic poly(orthoester) core will allow preparation of systems with significantly enhanced entrapment efficiency relative to other biodegradable segments such as poly(L-lactic-co-glycolic acid) copolymers.

While any of the anticancer agents that can form micellar complexes are suitable for this use, anticancer agents that are particularly suitable for micellar tumor targeting are those with low water solubility or high aromatic content, such as the anthracycline antibiotics (e.g. doxorubicin, daunorubicin, and epirubicin), mitomycin C, paclitaxel and its analogs (e.g. docetaxol), platinum analogs (e.g. cisplatin and carboplatin), and the like. Other agents may include anticancer proteins, such as neocarzinostatin, L-asparaginase, and the like, and photosensitizers used in photodynamic therapy.

2. Bioerodible Block Copolymer Matrix for Controlled Drug Delivery

In the block copolymers of this invention, phase separation will occur where domains of the B block form within the continuous A-phase or vice versa. Such phase-separated material will have unique and useful thermal properties. Specifically, unlike poly(orthoesters) containing short segments of PEG within the poly(orthoester), which when heated will gradually soften, PEG/POE AB, ABA, or BAB block copolymers have relatively sharp melting points. Further, while poly(orthoesters) containing short segments of poly(ethylene glycol) that have low softening temperatures have very poor mechanical properties, the copolymers of this invention, even those having very low melting temperatures, will retain mechanical properties suitable for use as implants.

To use the copolymer as a sustained-release vehicle, the active agent must be incorporated into a matrix of the copolymer or encapsulated within a capsule (or a "microcapsule" or "nanocapsule", as those terms are sometimes used) of the copolymer. Methods for the preparation of sustained-release dosage forms using biodegradable polymers are well known in the art, as discussed in the references cited in the "BACKGROUND OF THE INVENTION" section of this application, and in other references familiar to those of ordinary skill in the art; so that a person of ordinary skill in the art would have no difficulty, having regard to that skill and this disclosure, in preparing sustained-release formulations using the copolymer of this invention. Suitable active agents include therapeutic agents such as pharmaceutical or pharmacological active agents, e.g. drugs and medicaments, as well as prophylactic agents, diagnostic agents, and other chemicals or materials useful in preventing or treating disease. The compositions of this invention are particularly useful for the therapeutic treatment of humans and other mammals, but may also be used for other animals. In addition, the sustained-release compositions of this invention may also be used for the release of cosmetic and agricultural agents, or for the release of biocides, such as fungicides or other pesticides, into an environment where prolonged release of the active agent is desired.

In the case of matrix formulations, the copolymer is first mixed with the active agent. High homogeneity may be achieved by mixing the polymer in its heat softened state with the active agent, followed by lowering the temperature to harden the composition. Alternatively, the copolymer can be dissolved in an appropriate casting solvent, such as tetrahydrofuran, methylene chloride, chloroform or ethyl acetate, and the active agent can then be dispersed or dissolved in the copolymer solution, followed by evaporating the solvent to achieve the finished composition. Another method is grinding a solid copolymer material into powder which is then mixed with a powdered active agent. The active agent may also be incorporated into the mixture of monomers before polymerization provided that it is stable under the polymerization conditions and does not interfere with the polymerization reaction.

If the active agent is one that is unstable at elevated temperatures (e.g. above 40° C.), or in the presence of organic solvents or organic solvent/water mixtures, such as a protein, then special preparation techniques may be required to minimize the exposure of the active agent to damaging conditions. Such techniques are disclosed in, for example, U.S. Pat. No. 5,620,697 (Törmälä et al., assigned to Orion-Yhtyma Oy and Leiras Oy), which discloses ultrasonic melting to form matrix-type pharmaceutical compositions, and U.S. Pat. No. 5,518,730 (Fuisz, assigned to Fuisz Technologies, Inc.), which discloses melt-spinning, both of which techniques are designed to minimize the exposure of the polymer and active to elevated temperatures. Other methods are disclosed in the documents cited elsewhere in this application.

An alternate method for the incorporation and release of sensitive therapeutic agents is to use bioerodible copolymers that have physical properties tailored for this incorporation. For example, the copolymer may be chosen so that it is semi-solid and has an ointment-like consistency, rather than being fully solid. Thus, a copolymer may be chosen that has a very high viscosity at normal body temperature of 37° C. so that little if any deformation takes place at that temperature. However, the viscosity of the copolymer may decrease substantially at temperatures no higher than 45° C., or preferably by 40° C., so that injection of the material may be possible at a temperature at which the active agent retains its activity.

The composition obtained from any of the above methods can be readily processed into a variety of shapes and forms for implantation, insertion or placement on the body or into body cavities or passageways. For example, the copolymer composition may be injection molded, extruded or compressed into a thin film or made into devices of various geometric shapes or forms such as flat, square, round, cylindrical, tubular, disc, ring and the like. Rod- or pellet-shaped devices may be implanted through a trocar, such as is known for Norplant® implants, and these or other shapes may be implanted by minor surgical procedures. Alternatively, a device may be implanted following a major surgical procedure such as tumor removal in the surgical treatment of cancer. The implantation of polymer wafers containing anticancer agents is described, for example, in Brem et al., U.S. Pat. Nos. 5,626,862 and 5,651,986, and references cited therein; and the copolymers of this invention will find utility in such applications.

The polymer composition may also be injected by syringe subcutaneously or intramuscularly as particles of 0.1 $\mu$m to 1000 $\mu$m, preferably 0.5 $\mu$m to 200 $\mu$m, and more preferably 1 $\mu$m to 150 $\mu$m suspended in a pharmaceutically acceptable injection base. Liquid vehicles useful for suspending the drug-copolymer composition for injection include isotonic saline solution or oils (such as corn oil, cottonseed oil, peanut oil and sesame oil) which, if desired, may contain other adjuvants.

Another injectable dosage form may be prepared from an active agent mixed in with a copolymer of the present invention which has an ointment-like consistency. Such a dosage form may be administered by injection with or without a solvent.

The copolymer composition administered by either injection or implantation undergoes bioerosion in the body into non-toxic and non-reactive materials. By controlling the number of hydrolyzable bonds in the polymer, the active agent may be released at a desired rate. Implants prepared from the present copolymers in which the copolymer constitutes the matrix containing an active agent also have the advantage that they do not require removal because of the bioerodibility of the copolymer.

In some cases, particles with cores of the pure active agent coated with various thicknesses of the present copolymer may be preferred for sustained delivery of the active agent. Coating or encapsulation of discrete particles of the active agent may be accomplished by conventional methods which are all well-known to the person skilled in the art. For example, finely divided drug particles may be suspended in a solvent system (in which the drug is not soluble) containing the dissolved copolymer and other excipients, followed by spray drying. Alternatively, the drug particles may be placed in a rotating pan or a fluid-bed dryer and the copolymer dissolved in a carrier solvent is sprayed onto the drug particles until a suitable coating quantity is deposited on the particles to give a desired thickness. The coating may also be achieved by suspending the drug particles in a solvent system containing the dissolved copolymer followed by adding to the suspension a non-solvent causing the copolymer to precipitate and form a coating over the drug particles.

For the sustained release compositions, because the active agent will be released over a controlled period of time, the agent usually is present in an amount which is greater than the conventional single dose. The relative proportions of the active agent and the copolymer can vary over a wide range (e.g., 0.1 to 50 weight percent) depending on the therapeutic agent and the desired effect.

Sustained compositions of cosmetic and agricultural agents may also be prepared by any one of the methods as described above, using the copolymers of the present invention.

The solid copolymers are also useful for a variety of orthopedic applications. For example, they can be used as fracture fixation devices for repair of osteochondral defects, ligament and tendon reconstructions and bone substitutes. In addition, the fact that the present copolymers permit simultaneous selection of both a desired level of their mechanophysical state and a desired rate of bioerodibility, also renders them attractive as grafts or scaffolds on which cells can be cultured in vitro prior to implantation to regenerate tissues. Tissues which can be regenerated using this approach include but are not limited to bone, tendon, cartilage, ligaments, liver, intestine, ureter and skin tissues. For example, the copolymers may be used to regenerate skin for patients with burns or skin ulcers. Cartilages may be repaired by first isolating chondrocytes from a patient (or a donor), allowing them to proliferate on the scaffolds prepared from the present copolymer and re-implanting the cells in the patient.

The copolymer scaffolds or implants may further contain other biologically active substances or synthetic inorganic materials such as reinforcing filler material for enhancing the mechanical properties of the scaffolds or implants (e.g. calcium sodium metaphosphate fibers), antibiotics, or bone growth factors to induce and/or promote orthopedic restoration and tissue regeneration.

PREPARATIONS AND EXAMPLES

Preparation 1: Preparation of a diketene acetal of formula IV 3,9-Di(ethylidene)-2,4,8,10-tetraoxaspiro[5.5]undecane (DETOSU)

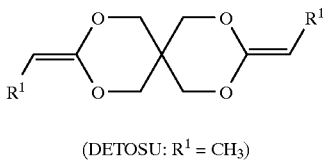

(DETOSU: $R^1$ = $CH_3$)

A 3-liter, 3-necked flask fitted with a mechanical stirrer, argon inlet tube, thermometer and rubber septum was charged with 1.2 L ethylenediamine. The flask was cooled with ice water and the contents kept at about 8° C. under an argon atmosphere. A hexane solution of n-butyllithium, 130 g (2 mol n-BuLi), was added over one hour through a stainless steel U-tube pushed through the rubber septum, using carefully controlled argon pressure. Next, a mixture of 3,9-divinyl-2,4,8,10-tetraoxa-spiro[5.5]undecane, 530 g (2.5 mol), (available from Aldrich Chemical Company, Inc., Milwaukee, Wis., USA) and 0.5 L ethylenediamine was cooled to 8° C. and added to the flask. After stirring at 8° C. for 3 hours, the reaction mixture was poured into 3 L of ice water with vigorous stirring. The aqueous mixture was extracted twice with 1 L portions of hexane. The combined hexane extracts were washed three times with 1 L portions of water, dried over anhydrous magnesium sulfate and filtered under suction. The filtrate was evaporated to dryness on a rotary evaporator to give crude material (413 g, 78%) containing 90% DETOSU.

The crude DETOSU product was dissolved in 2 L hexane containing 10 mL triethylamine and the solution was placed in a 4 L filter flask, sealed, and stored in a freezer at −20° C. for two days. The crystals thus formed were collected by basket centrifugation at −5° C. under an argon atmosphere. Distillation of the brownish product through a 12-inch Vigreaux column at reduced pressure gave 313 g (61% yield) DETOSU as a colorless liquid, boiling point 82° C. (0.1 Torr), which crystallized at room temperature, with a melting point of 30° C. and a characteristic infrared absorption band at 1700 $cm^{-1}$.

Preparation 2: Preparation of diols of formula III(a), III(b) or III(c)

P2(a).

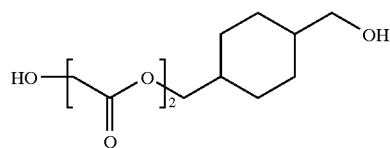

Under anhydrous conditions, 14.42 g (100 mmol) CDM and 11.6 g (100 mmol) glycolide were weighed into a 100-mL round bottom flask. The flask was stoppered with a rubber septum, then heated in an oil bath at 180° C. for 24 hours. The product shown above was obtained as a viscous oil.

P2(b).

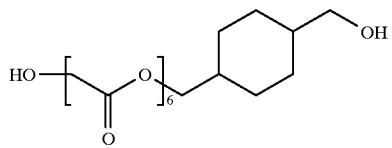

CDM, 2.88 g (20 mmol) and 6.96 g (60 mmol) glycolide were reacted according to the procedure of Preparation P2(a), yielding the product shown above as a low-melting solid.

The following additional diols were synthesized using analogous procedures: P2(c).

P2(c).

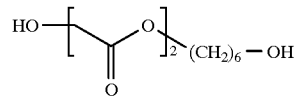

P2(d).

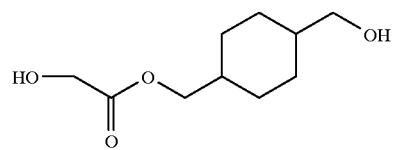

Other diols are similarly synthesized using analogous procedures.

Example 1

Preparation of diblock copolymers of formula I

E1(a).

In a glove box, PEG 2000 methyl ether, 4 g (2 mmol), was weighed into a 100 mL flask and dissolved in 25 g THF, and 4.372 g (20.6 mmol) DETOSU was added. Three drops of a 25 mg/mL solution of PTSA in THF were added to the solution, and the flask was capped with a rubber septum and heated in an oil bath at 70° C. for 30 minutes. A further three drops of PTSA solution were added, and the solution heated for a further 30 minutes. CDM, 2.596 g (18 mmol), was added, and the solution stirred until all CDM dissolved, when another three drops of PTSA solution were added. After stirring for 30 minutes, the solution was transferred to an addition funnel and dropped into approximately 1 L hexane with vigorous stirring to precipitate the diblock copolymer, which was filtered and dried in a vacuum oven. The isolated copolymer had a number average molecular weight, $M_n$, of 12240, indicating the presence of an average of 3 1 orthoester units in the molecule, n=31, and contained approximately 36.5% PEG. The copolymer had a melting point of 34.1° C. and a glass transition temperature, $T_g$, of 27.5° C.

E1(b).

A similar reaction using 10 g (2 mmol) PEG 5000 methyl ether gave a diblock copolymer having an $M_n$ of 14820, a PEG content of 58.9%, and a melting point of 51.2° C.

E1(c).

A similar reaction using 7 g (1.4 mmol) PEG 5000 methyl ether and 2.682 g (18.6 mmol) CDM gave a diblock copolymer having an $M_n$ of 19150, a PEG content of 49.8%, a melting point of 48.2° C., and a $T_g$ of 32.7° C.

E1(d).

A similar reaction using 20 g (4 mmol) PEG 5000 methyl ether and 2.307 g (16 mmol) CDM gave a diblock copolymer.

Example 2

Preparation of triblock copolymers of formula II

In a glove box, 4.372 g (20.6 mmol) DETOSU and 2.307 g (16 mmol) CDM are weighed into a 100 mL flask and dissolved in 25 mL THF. One drop of a 25 mg/mL solution of PTSA in THF is added to initiate the reaction. When the reaction mixture has cooled to room temperature, 8 g (4 mmol) PEG 2000 is added. The solution is gently warmed until all the PEG has fully dissolved, and three drops of the PTSA solution are added. The flask is capped with a rubber septum and heated in an oil bath at 70° C. for 30 minutes. A further three drops of the PTSA solution are added and the flask heated for an additional 30 minutes. After cooling to room temperature, the solution is added dropwise to 1 L hexane with stirring to precipitate the triblock copolymer. The copolymer is dried in a vacuum oven.

Example 3

Solubility of the copolymers

The copolymer of E1(d), 100 mg, was dissolved in 2 mL acetone, and 20 mL phosphate-buffered saline, pH 7.4, was added. No precipitation of the copolymer was observed. The solution was placed under aspirator vacuum at room temperature to remove the acetone, and the copolymer remained in solution.

Other copolymers of formula I and formula II show similar solubility.

Example 4

Solubilization of hydrophobic/water-insoluble active agents

The copolymer of E1(d), 100 mg, was dissolved in 2 mL acetone, and the solution added to a solution of 7.7 mg hydrocortisone in 2 mL acetone. The combined acetone solutions were added to 5 mL phosphate-buffered saline, pH 7.4, the acetone removed under vacuum, and the aqueous solution filtered through a 0.45 μm filter. The aqueous solution was found to have a hydrocortisone concentration of 1.1 mg/mL, approximately four times greater than the water solubility of hydrocortisone of 0.28 mg/mL, indicating micellar encapsulation and solubilization of the hydrocortisone by the copolymer.

Other copolymers of formula I and formula II show similar solubilization of hydrophobic/water-insoluble active agents.

Example 5

Bioerodibility of the copolymers

The copolymer of E1(c) was pressed at 48° C. and 1000 atm into a slab 0.6 mm thick, and the slab then cut into wafers approximately 6 mm×6 mm. The wafers were weighed, and then placed into phosphate-buffered saline, pH 7.4, at 37° C.; and the weight loss of the wafers measured as a function of time. The results are shown in FIG. 1.

Other copolymers of formula I, II, and III show similar bioerodibility.

While this invention has been described in conjunction with specific embodiments and examples, it will be evident to one of ordinary skill in the art, having regard to this disclosure, that equivalents of the specifically disclosed materials and techniques will also be applicable to this invention; and such equivalents are intended to be included within the following claims.

What is claimed is:

1. A block copolymer of formula I:

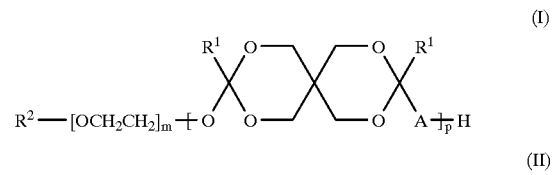

formula II:

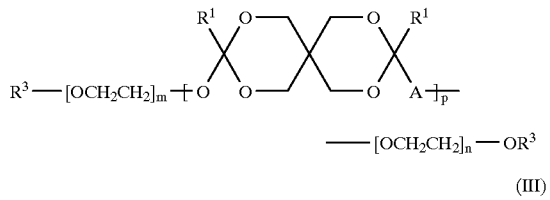

or formula III:

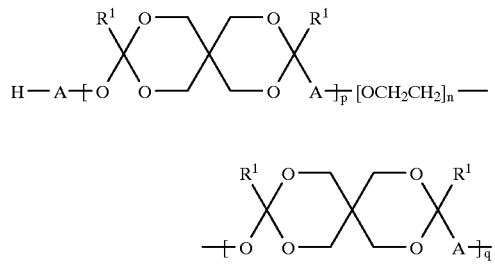

in which:

m and n are independently an integer from 5 to 500;

p and q are independently an integer from 5 to 100;

$R^1$ and $R^2$ are independently $C_1$–$C_4$ alkyl;

$R^3$ is H or $C_1$–$C_4$ alkyl; and

A is —O—$R^4$—, —O—$R^1$—, or a mixture thereof, where:

$R^4$ is selected from

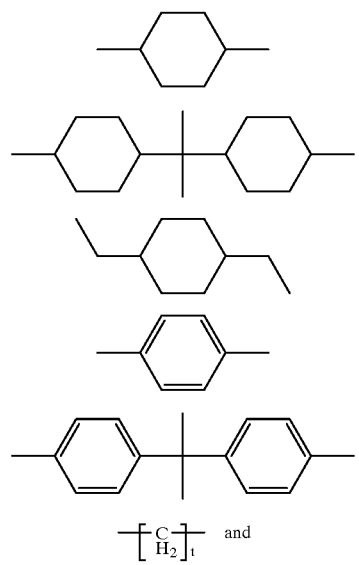

-continued

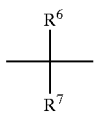

where t is an integer from 1 to 12,
$R^6$ is $C_1$–$C_4$ alkyl, and
$R^7$ is H or $C_1$–$C_4$ alkyl; and
$R^5$ is

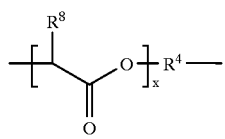

in which:
x is an integer from 1 to 10, and
$R^8$ is H or $C_1$–$C_6$ alkyl.

2. The copolymer of claim 1 which is a compound of formula I.

3. The copolymer of claim 2 where m is an integer from 50 to 250, and p is an integer from 10 to 50.

4. The copolymer of claim 2 where $R^1$ is ethyl and $R^2$ is methyl.

5. The copolymer of claim 2 where A is —O—$R^4$— and HO—$R^4$—OH is cyclohexanedimethanol.

6. The copolymer of claim 1 which is a compound of formula II.

7. The copolymer of claim 6 where m and n are independently an integer from 50 to 250, and p is an integer from 10 to 50.

8. The copolymer of claim 6 where $R^1$ is ethyl and $R^3$ is hydrogen or methyl.

9. The copolymer of claim 6 where A is —O—$R^4$— and HO—$R^4$—OH is cyclohexanedimethanol.

10. The copolymer of claim 1 which is a compound of formula III.

11. The copolymer of claim 10 where n is an integer from 50 to 250, and p and q are independently an integer from 10 to 50.

12. The copolymer of claim 10 where $R^1$ is ethyl.

13. The copolymer of claim 10 where A is —O—$R^4$— and HO—$R^4$—OH is cyclohexanedimethanol.

14. A micellar pharmaceutical composition for the delivery of a hydrophobic or water-insoluble active agent, comprising the active agent physically entrapped within but not covalently bonded to a drug carrier comprising a block copolymer of claim 1.

15. A micellar pharmaceutical composition for the delivery of a hydrophobic or water-insoluble active agent, comprising the active agent physically entrapped within but not covalently bonded to a drug carrier comprising a block copolymer of claim 2.

16. The composition of claim 15 where the active agent is an anticancer agent.

17. A composition for the sustained release of an active agent, comprising the active agent dispersed in a matrix comprising the block copolymer of claim 1.

18. The composition of claim 17 where the active agent is an anticancer agent.

19. A composition for the sustained release of an active agent, comprising the active agent dispersed in a matrix comprising the block copolymer of claim 2.

20. The composition of claim 19 where the active agent is an anticancer agent.

* * * * *

UNITED STATES PATENT AND TRADEMARK OFFICE
CERTIFICATE OF CORRECTION

PATENT NO. : 5,939,453
DATED : Aug. 17, 1999
INVENTOR(S) : Heller et al.

It is certified that error appears in the above-identified patent and that said Letters Patent is hereby corrected as shown below:

Claim 1, column 18, line 41 "—O—$R^1$—" should read -- —O—$R^5$— --.

Signed and Sealed this

Eighth Day of February, 2000

Attest:

Attesting Officer

Q. TODD DICKINSON
Commissioner of Patents and Trademarks